US011791040B2

(12) United States Patent
Falk et al.

(10) Patent No.: US 11,791,040 B2
(45) Date of Patent: Oct. 17, 2023

(54) NEONATAL CARE SYSTEM AND METHOD OF TRACKING COMPOSITION THEREOF

(71) Applicant: GE Precision Healthcare LLC, Wauwatosa, WI (US)

(72) Inventors: Steven M. Falk, Laurel, MD (US); Daniel W. Medeiros, Brookfield, WI (US); Rajendra Naik, Bangalore (IN); Rajesh N. Kulkarni, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 318 days.

(21) Appl. No.: 17/189,999

(22) Filed: Mar. 2, 2021

(65) Prior Publication Data
US 2022/0285019 A1 Sep. 8, 2022

(51) Int. Cl.
*G16H 40/40* (2018.01)
*G06K 7/10* (2006.01)
*A61G 11/00* (2006.01)

(52) U.S. Cl.
CPC ........... *G16H 40/40* (2018.01); *A61G 11/005* (2013.01); *G06K 7/10366* (2013.01)

(58) Field of Classification Search
CPC .............. G16H 40/40; G06K 7/10366; A61G 11/00–11/009
See application file for complete search history.

(56) References Cited

U.S. PATENT DOCUMENTS

| | | | | |
|---|---|---|---|---|
| 2003/0197003 A1* | 10/2003 | Kneuer | .................. | A61G 11/00 219/494 |
| 2013/0289677 A1* | 10/2013 | Bharadwaj | ............. | A61G 11/00 607/100 |
| 2017/0199520 A1* | 7/2017 | Glatfelter | ............... | B64C 39/024 |
| 2018/0177656 A1* | 6/2018 | Giambattista | ......... | F26B 17/103 |

* cited by examiner

*Primary Examiner* — Samuel G Gilbert
(74) *Attorney, Agent, or Firm* — ANDRUS INTELLECTUAL PROPERTY LAW, LLP (57) ABSTRACT

A neonatal care system includes a platform for supporting an infant, a plurality of part tags each embedded in a part within the neonatal care device, and at least one part reader. Each of the plurality of part tags is configured to transmit a part identifier and the at least one part reader is configured to receive the part identifiers transmitted from the plurality of the part tags. A controller is configured to store at least one part identifier catalog, receive the part identifiers from the part reader, and compare the part identifiers generated by the plurality of part tags to the at least one part identifier catalog. If any of the received part identifiers does not match the at least one part identifier catalog, then an alert is generated.

19 Claims, 7 Drawing Sheets

NEONATAL CARE SYSTEM AND METHOD OF TRACKING COMPOSITION THEREOF

BACKGROUND

The present disclosure generally relates to neonatal care systems and methods, and more particularly to systems and methods for tracking parts within a neonatal care system, such as an incubator or a warmer.

Neonates, particularly premature infants, are often placed within an incubator so that they may have a controlled and monitored environment to aid in their survival and growth. Similarly, premature infants or infants needing medical attention may be placed in an infant warmer, such as a radiant warmer, for provision of medical therapies and/or procedures, and/or for monitoring a health status of the infant. Neonatal incubators, warmers, and other neonatal care systems include a platform for supporting an infant and a controlled environment. Neonatal care systems comprise many parts and typically require extensive cleaning processes between use with patients, including disassembly and cleaning of multiple parts. Many parts comprising a neonatal care system are reusable, removable, and cleanable. Other parts in use within the neonatal care system may be intended for single patient use and thus may be disposed of after use with a single infant. Still other parts may have a predefined life cycle, such as usable with a predefined number of patients or for a predefined operation of the neonatal care system.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a neonatal care system includes a platform for supporting an infant, a plurality of part tags each embedded in a part within the neonatal care device, and at least one part reader. Each of the plurality of part tags is configured to transmit a part identifier and the at least one part reader is configured to receive the part identifiers transmitted from the plurality of the part tags. A controller is configured to store at least one part identifier catalog, receive the part identifiers from the part reader, and compare the part identifiers generated by the plurality of part tags to the at least one part identifier catalog. If any of the received part identifiers is not on or does not match the at least one part identifier catalog, then an alert is generated.

In one embodiment, the part identifier catalog may include a plurality of part schedules and one or more of the part schedules may be selected for assessing the received part identifiers. In one such example, one or more part schedules may be selected based on a state of the neonatal care system, based on the detected part identifiers, or based on a time or order of detection of the part identifiers.

One embodiment of a method of tracking composition of a neonatal care device includes providing a plurality of part tags, each tag embedded in a part of the neonatal care system and configured to transmit a part identifier, and further providing at least one part reader configured to receive the part identifiers transmitted from the plurality of part tags, such as when the parts are properly placed or installed within the neonatal care system. The method of tracking composition of the neonatal care system further includes, at a controller, receiving the part identifiers at the at least one part reader and generating a present parts list for the neonatal care system representing all parts of the neonatal care system for which the part identifier is received by the at least one part reader within a period of time. The present parts list is stored in association with the specified period of time so as to track the composition of the neonatal care system over time.

Various other features, objects, and advantages of the invention will be made apparent from the following description taken together with the drawings.

DETAILED DESCRIPTION

Neonatal care systems are complicated systems comprising many components and parts that must be assembled correctly into the system to provide consistent performance quality and provide consistent and expected performance. The inventors have recognized that tracking systems and methods are needed for infant care systems, such as incubators and warmers, to ensure patient safety and configuration management. Often, parts of neonatal care systems get replaced by third party parts that have not been validated for use with the particular infant care system. This can create an unacceptable patient safety risk, as many parts within the infant care system must be tested and certified for performance within the environment of the infant care system, including for thermal performance, bio-compatibility, cytotoxicity, containment of volatile organic compounds, and particulate matter generation, to name a few. For example, a mattress used in a neonatal care system must be tested and validated for each of the foregoing performance metrics to certify that the construction and design of the mattress will operate well from a patient safety standpoint within the micro environment of the patient care system. Further, given that neonatal care systems must be disassembled and cleaned between patients, the inventors have recognized that problem exist with improper assembly after cleaning, including parts being omitted from the assembled neonatal care system and/or parts being improperly installed. Some neonatal care systems allow interchangeability of components and parts to create different configurations. The inventors have recognized that mistakes are made in assembling the various infant care system configurations, where improper combinations of parts may be utilized accidentally, which may create a patient safety risk. To provide just one example, some neonatal care systems have multiple size walls may be assembled around the platform and configured to hold the infant on the platform and within the infant care system. The inventors have recognized that improper assembly of wall combination occurs, where different sized walls are accidently used together on a single neonatal care system assembly. For example, tall walls may be used in combination with one shorter wall. A clinician caring for an infant may not realize this improper combination of the walls, given that the walls are clear and difficult to see, and thus may not take proper precautions on the side of the small wall to prevent the infant from falling out of the neonatal care system.

The inventors have further recognized that a problem exists where parts of the neonatal care system are not properly installed or used, thereby creating suboptimal performance of the neonatal care system, and even posing patient safety risks. For example, parts of the neonatal care system may be used without cleaning between patients or may be used for too long past their approved use. To provide just one example, an error filter within the neonatal care system needs to be changed at regular intervals and/or between patients. If the air filter is used for longer than it should be and/or not changed between a patient, then a risk is posed to the infant housed within that neonatal care system. Similarly, parts intended for single-patient use are sometimes reused for patients. Reuse of parts and accessories intended for one-time use can create health risks for the infant. For example, disposable covers intended for single patient use are not made to withstand cleaning processes and thus may degrade and be unsuitable after cleaning. The inventors have recognized that detection of multiple uses of one-time use parts would be beneficial. Similarly, the inventors have recognized that detection of use of a part without cleaning or use of an improper part for a given neonatal care system would also be beneficial. Similarly, detection of use of a recalled part and/or a part that is not certified for a particular neonatal care system should also be provided. Further still, the inventors have developed a system and method whereby proper installation and use of various parts within the neonatal care system, can be tracked and an alert generated if improper parts or uses are detected.

Further still, the inventors have recognized that significant problems exist in the relevant art with doors and walls of neonatal care systems not being properly installed or latched while an infant is housed within the system, thereby creating a risk that the neonate can fall out of the care system. Thus, the inventors have developed a system that can detect that the wall of the neonatal care system is not properly installed and/or that the door of the neonatal care system is not properly latched and can generate an alert accordingly.

As disclosed in detail herein, the inventors have developed apart tracking system for use in and with a neonatal care system that includes a plurality of part tags and at least one part reader. The plurality of part tags are embedded in parts within the neonatal care system. Each of the plurality of part tags is configured to transmit a part identifier received at one or more part readers positioned within the neonatal care system. A controller within the neonatal care system is configured to track the various parts via the received part identifiers and to determine that all detected parts are permitted for the particular neonatal care system and that all necessary parts for the particular neonatal care system are present. In some embodiments, the system may further be configured to determine whether the parts present on the neonatal care system comply with expected part combinations such that the parts are intended to be used together to form a predefined configuration for the neonatal care system. If any of various alert conditions are met, such as unpermitted parts being used, necessary parts being omitted, unexpected part combinations being present, or the like, then the system may be configured to generate an alert to alert the clinician of the problem.

In certain embodiments, the plurality of part tags are each radio-frequency identification (RFID) tags and the part reader is an RFID reader. In various embodiments, the plurality of part tags may be passive or active RFID tags, and a corresponding RFID reader provided.

Figure 1:
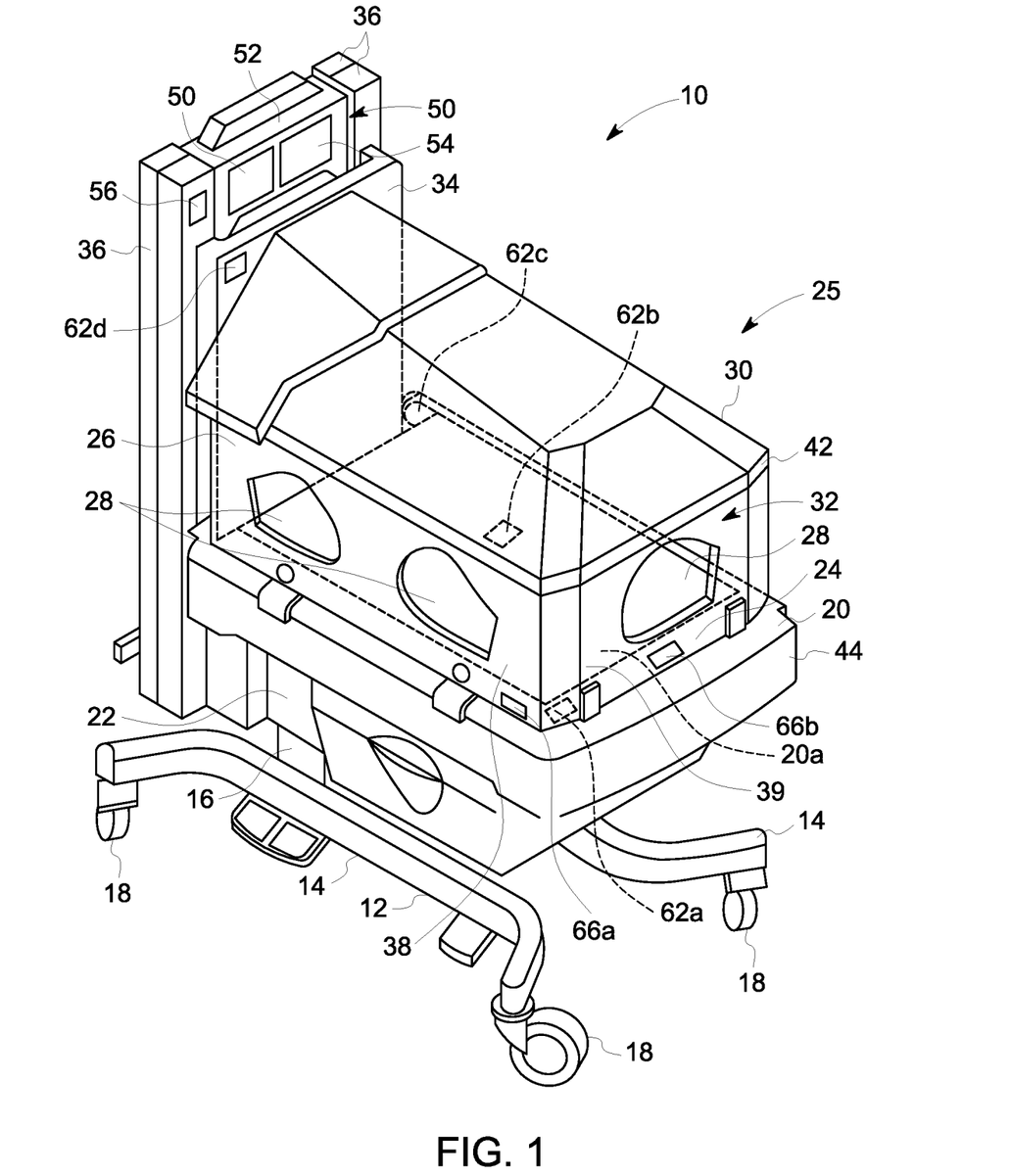
FIG. 1 is a perspective view of a neonatal care system in accordance with an embodiment of the disclosure.

FIG. 1 is a perspective view of a neonatal care system 10 in accordance with an embodiment of the disclosure. The neonatal care system 10 depicted in FIG. 1 is a hybrid incubator/warmer; however, it should be appreciated that other types of neonatal care system 10 are envisioned. For example, the neonatal care system 10 may be an infant warmer, an infant incubator, or any other device configured to provide a controlled environment for a neonate.

The neonatal care system 10 includes a base 12 comprising a pair of U-shaped members 14 that are joined together and which provide support for a vertical base member 16. Wheels 18 may provide for ready movement of the neonatal care system 10. A chassis 44 provides a platform 20 which supports an infant in the neonatal care system 10. The platform 20 includes a flat, planar surface 24 that underlies the infant mattress or other bedding when positioned with the neonatal care system 10. The platform 20 may comprise a bedding receiving area configured to receive a mattress or a bedding system for a neonate. Multiple types of bedding systems may be available, thus providing an adaptable care system 10 that can be adapted to various neonatal care needs. The chassis 44 may be mounted to a movable portion 22 of the vertical base member 16 in a manner such that the user can adjust the height of the platform 20 by raising and lowering the movable vertical base member 22 with respect to the stationary vertical base member 16 to the preferred height by the user.

Extending upwardly around the periphery of the platform 20 is a housing 25 which forms the warming compartment 32 and also protects the infant and maintains it on the platform 20. The housing 25 includes a plurality of walls 26, normally of a transparent plastic material and which surround the planar surface 24 to enclose the infant on the planar surface 24. The walls 26 can have handholes 28 to enable the caregiver to reach the infant. The walls 26 include two side walls 38 and two end walls 39 mated or otherwise connected together so as to form a perimeter around the warming compartment 32. One or both of the side walls 38 may be openable or movable to provide further access to an infant, at least one of the side walls 38 can be dropped downwardly to open fully for complete access to the infant, to provide care and for taking the infant in and out of the neonatal care system 10.

In some embodiments, the housing 25 also includes a hood 30. In the embodiment of FIG. 1, the hood 30 can be raised and lowered vertically to cover and uncover the warming compartment 32. The hood 30 may be affixed to a movable vertical frame member 34 that moves with respect to and fits with stationary vertical frame member 36. When in the position shown in FIG. 1, the hood 30 may abut the upper peripheral edges 42 of the walls 26 to enclose therein an infant warming compartment 32 and provide a controlled environment, a microenvironment, where heat and humidity can be controlled to aid in the development and wellbeing of the infant. A lifting mechanism (not shown) is used to move the movable vertical frame members 34 and the hood 30 upwardly and downwardly with respect to the stationary vertical frame members 36. In other embodiments, the hood 30 may be stationary, which is common for incubator arrangement where the hood 300 connects to the walls to provide a complete enclosure and in a radiant warmer where the hood is typically in a stationary position above the platform and is disconnected from the walls.

A radiant heater (not shown) can also be included for providing heat to the infant when the hood 30 is in its uppermost position and thus the neonatal care system 10 can be operated in the manner of an infant warmer or as an incubator in the configured position as shown in the present FIG. 1. The controller 50 may be housed anywhere on or near the system 10, such as positioned in frame housing 52 between the stationary vertical frame members 36 includes a processor and storage to store data and programs. The controller 50 be operatively connected to a display 54 to display visual summaries of various monitored physiological parameters as well as control parameters for the neonatal care system 10. For example, the display 54 may display patient physiological parameters such as Sp02, FiO2, or temperature; physiological and system alarms; microenvironmental parameters such as temperature or humidity; caregiver queries or prompts; or other information related to the neonatal care system, the infant care system, the infant or the care setting. The display 54 may be further configured to display information relating to the part tracking system 60, including any alerts generated thereby. The frame housing 52 may also contain a speaker 56 to generate sound and communicatively connected to the controller 50, such as for performing audio alerts generated by the part tracking system. It should be appreciated that the neonatal care system 10 may comprise more than one display 54.

Figure 2:
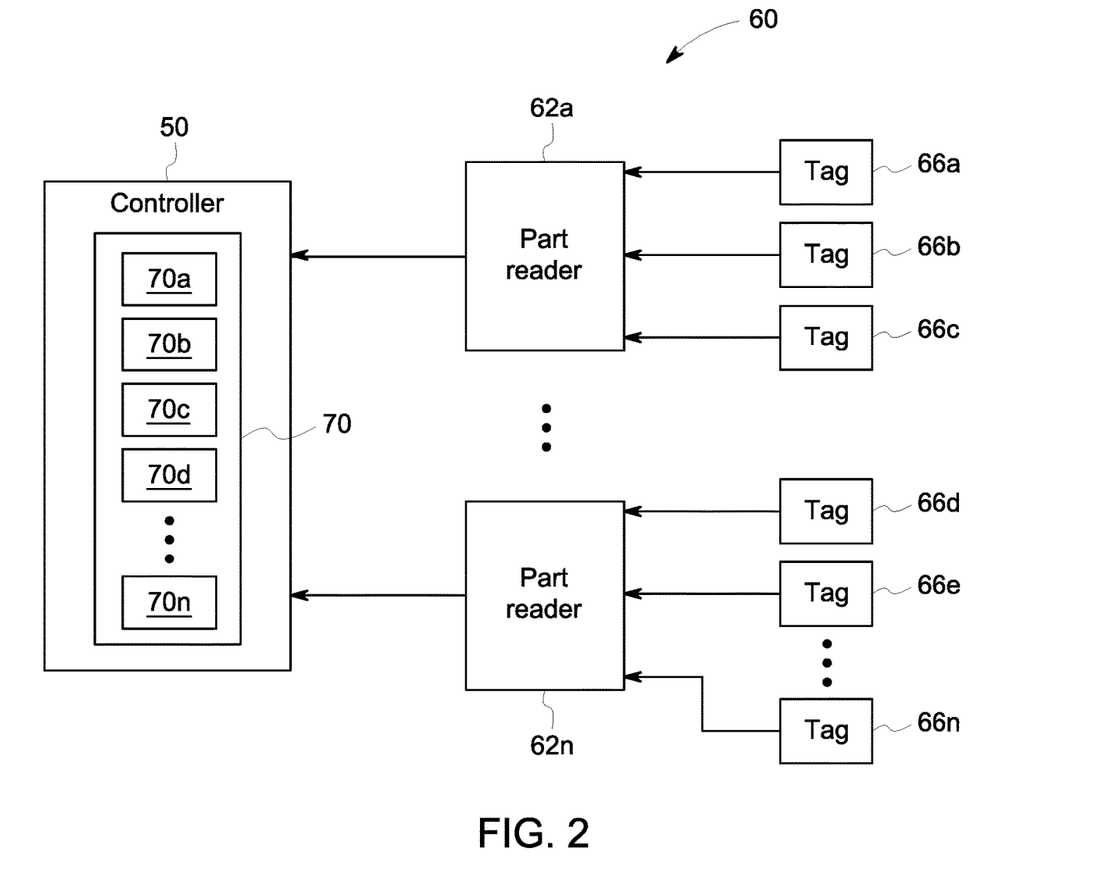
FIG. 2 is a schematic diagram of a part tracking system within a neonatal care system in accordance with an embodiment of the disclosure.

A part tracking system for the neonatal care system 10 includes a plurality of part readers 62a-62d positioned at locations within the system 10 and configured to receive wireless communications from a plurality of part tags 66a-66b that are affixed on or embedded in parts of the neonatal care system 10. FIG. 2 is a schematic diagram of a part tracking system 60. It includes a plurality of part readers 62a-62n that each receive communications from a plurality of part tags 66a-66d. The tags 66a-66n are incorporated in and/or positioned on various parts of the neonatal care system 10. The readers 62a-62n are configured and positioned to receive wireless communication from the tags 66a-66n, such that wireless transmissions from each tag 66a-66n on a part that is properly assembled or incorporated in the system 10 is received by at least one of the plurality of readers 62a-62n. Each tag 66a-66n is configured to communicate a part identifier, which is a code (e.g., numeric or alpha numeric) identifying the part to which it is attached or incorporated. The tag may also be configured to transmit a tag identifier identifying itself and/or an authentication key to authenticate the tag within the system 60. The readers 62a-62n thus receive signals that indicate the presence of each tagged part when present within the system 10 and, as explained in more detail below, may be configured to determine whether each tagged part is properly installed and/or in proper use within the system.

In certain embodiments, the plurality of part tags are each radio-frequency identification (RFID) tags and the part reader is an RFID reader. In various embodiments, the plurality of part tags may be passive or active RFID tags, and a corresponding RFID reader provided. In other embodiments, different communication frequencies and protocols may be used for facilitating wireless communication between the plurality of tags and the at least one reader, such as Bluetooth, BLE, ANT, NFC, to name a few.

Each reader 62a-62n is communicatively connected to the controller 50, which may be a wired or wireless connection and utilize a corresponding communication protocol. The controller 50 receives the part identifiers and/or other part identification information generated by the part readers 62a-62n upon receipt of the part identifiers from the respective part tags 66a-66n. The controller 50 is programmed and configured to track the reporting parts via the received information and to determine various information based thereon, such as whether all parts on the present incubator are permitted parts, whether all necessary parts for safe use are present, whether the combination of parts on the incubator represents an expected part combination, or the like. Alternatively or additionally, the controller 50 may be configured to track the order of assembly or disassembly of the parts on the system 10 and/or how long between insertion and removal (or vice versa) of each part, such as to track compliance with cleaning and/or assembly routines.

To facilitate such functionality, the controller 50 is configured to access one or more part identifier catalogs 70 including various schedules 70a-70n—which may each be a list, table, map, or any other data structure containing part identifiers or other part-related information. The controller 50 may have an internal memory configured to store the part catalog 70 or is otherwise configured to access a storage device storing the part catalog 70. The controller 50 is configured to compare the received part identifiers to the at least one part identifier catalog 70, such as comparing at least one of the part identifiers to one of the schedules 70a-70n and conduct analysis based thereon. The at least one part catalog 70 may include, for example, a permitted part schedule 70a, a necessary part schedule 70b, a part combinations schedule 70c, a cleaning schedule 70d, and/or any other schedule or other part-related information configured and stored for tracking composition of the neonatal care system 10.

The part identifier catalogs 70 may include, for example, a list of permitted part identifiers which list all part identifiers associated with parts that have been approved for use with the particular neonatal care system 10. The controller 50 may be configured to compare the received part identifiers to the permitted parts schedule 70a, such as a list of permitted parts or other data structure representing parts that are approved for the system 10, to confirm that all parts present are allowable for the particular type of neonatal care system 10. If a part identifier or other communication, such as an unknown RFID tag, communicates and is detected by the receiver, then an unpermitted part alert may be generated. For example, parts not appropriate for the particular neonatal care system may be utilized, such as a wrong mattress type or incubator wall type. The inappropriate part may be identified, and then a corresponding alert may be generated. Such information may also be logged by the controller 50 so that it is available for later analysis.

Alternatively or additionally, the received part identifiers from the tags 60a-60n may be compared to one or more necessary parts schedule 70b. The necessary parts schedule 70b may be, for example, a list or other data structure providing one or more sets of part identifiers that should be present for safe use of the neonatal care system 10. For instance, the necessary parts schedule 70b may comprise one or more lists containing sets of parts, each including one or more mattress part identifiers. If no part identifier associated with a mattress 47 (see FIG. 4) is identified within the system 10, then an alert may be generated to notify the clinician of the absence of the mattress. Thus, where a mattress is utilized that does not contain the appropriate tag, or perhaps does not contain any tag, the mattress alert will notify a clinician that the mattress is inappropriate. Likewise, such information may be logged to track the absence of the appropriate mattress or a permitted mattress.

Alternatively or additionally, the part identifiers received at each reader 62 may be compared to a part combinations schedule 70c. The part combinations schedule 70c for the neonatal care system 10 is configured to capture various configurations of the neonatal care system that are permitted and pre-approved, and thus represent proper use of the neonatal care system for housing an infant. Thus, for example, the part combinations schedule 70c may be a set of lists or other data structure providing sets of part identifiers representing expected part combinations, or groups of parts that are known to work together for assembling aspects of the neonatal care system 10.

For instance, part combinations schedule 70c may include combinations representing approved bed assemblies comprising various parts configured to operate together to provide an approved neonatal care bed configuration for the system 10. As another example, the part combinations schedule 70c may include a set of part identifiers identifying appropriate wall and/or hood combinations, as illustrated in the examples at FIGS. 3-5. In still other examples, the part combinations schedule 70c may represent other combinations of parts comprising known, approved, or acceptable arrangements of parts for aspects of the neonatal care system 10, or for the system 10 as a whole. The received part identifiers are compared to the one or more part combinations schedule 70c to determine whether the various detected parts on the system 10 match the schedule 70c, meaning that the combination of parts on the system 10 is represented in the schedule 70c. If not, then an abnormal combination is detected and the user can be alerted accordingly. Likewise, the abnormal part combination can be logged for documentation purposes.

Alternatively or additionally, the part identifiers received at each reader 62 may be compared to a cleaning schedule 70d. The cleaning schedule 70d includes information related to cleaning the neonatal care system 10 or any part thereof. For example, the cleaning schedule 70d may include a maximum use time for one or more parts representing a maximum amount of time that a part should be used between cleaning or between replacement. For example, if a part is a reusable part, then the controller may be configured to track removal of the part for cleaning and subsequent replacement thereof according to the cleaning schedule 70d. Alternatively or additionally, if a part is a disposable part, the controller 50 may be configured to track replacement of the respective part prior to the maximum use time therefore, which will be indicated by detection of a new part tag 66 for that part. Alternatively or additionally, the cleaning schedule 70d may include an order of part cleaning, such as during a cleaning mode or cleaning state for the neonatal care system, as described in more detail below.

The controller 50 may be configured to generate a present parts list based on the received part identifiers from the various tags 66a-66n. The present parts list for the neonatal care system 10 represents all parts of the neonatal care system for which a transmitted part identifier is received and recognized by the part readers 62a-62b in the part tracking system 60 within a defined period of time. For example, the defined period of time may be part identifiers received within a time window of a few seconds or minutes, or an appropriate time period in order to collect all the part identifiers transmitted from the various tags 66a-66n. Alternatively, the defined period of time may represent a care period, such as while the neonatal care system 10 is in use carrying for a particular patient. In still other embodiments, the defined period of time may be a tracking period, such as within a time window of one hour, one day, one week, etc.

For example, the system may be configured to energize the passive tags 66a-66n at regular intervals and to record the part identifiers transmitted therefrom in order to log the various parts present within the system at that defined time, which then gets compared to the part identifier catalog 70.

In addition to logging the present parts list and catalog comparisons at each defined period of time, the system may likewise be configured to generate an alert. If any of the part identifiers is not on the part identifier catalogs 70 and the comparison reveals any unpermitted parts, missing parts, or abnormal part combinations, then a corresponding alert may be generated. The alerts may be generated via the display 54 and/or the speaker 56 associated with the system 10 or may be generated by any user interface device associated with or receiving communication directly or indirectly from the controller 50. In certain examples, the alerts may be generated from a central monitoring station displaying information regarding multiple neonatal care systems 10 and/or may be sent to handheld devices for one or more clinicians, such as via applications on cellphones or other personal computing devices for one or more clinicians. The alerts may provide contextual help to a clinician or technician, such as making sure that the neonatal care system 10 is assembled properly and is used properly. As described herein, various types of alerts may be generated, such as the unpermitted part alert, missing part alert, and abnormal part combination alert, a cleaning alert, or various other alert types, examples of which are described herein.

Figure 3:
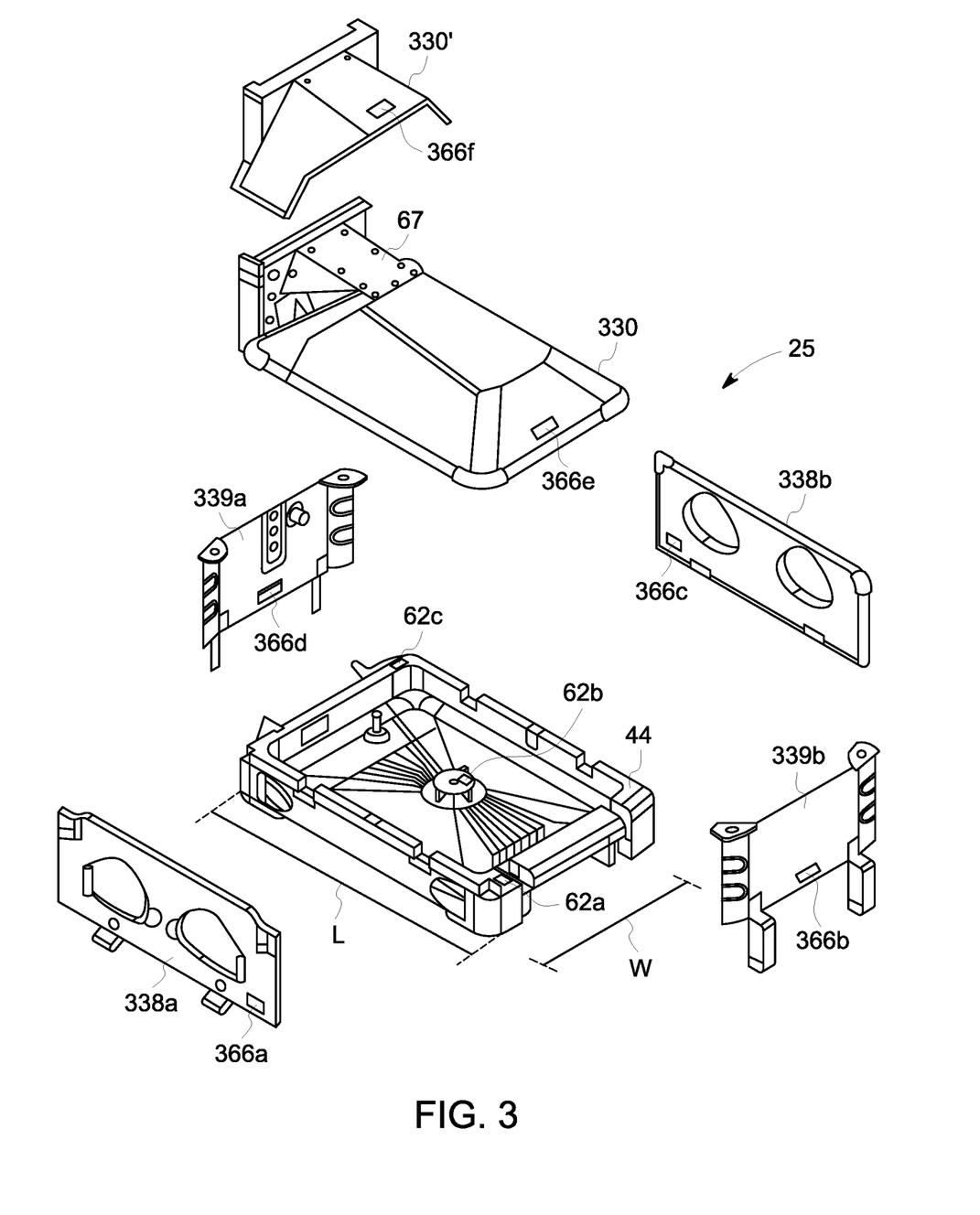
FIGS. 3-5 are exploded views showing various exemplary parts for a neonatal care system, each part having a part tag.
Figure 4:
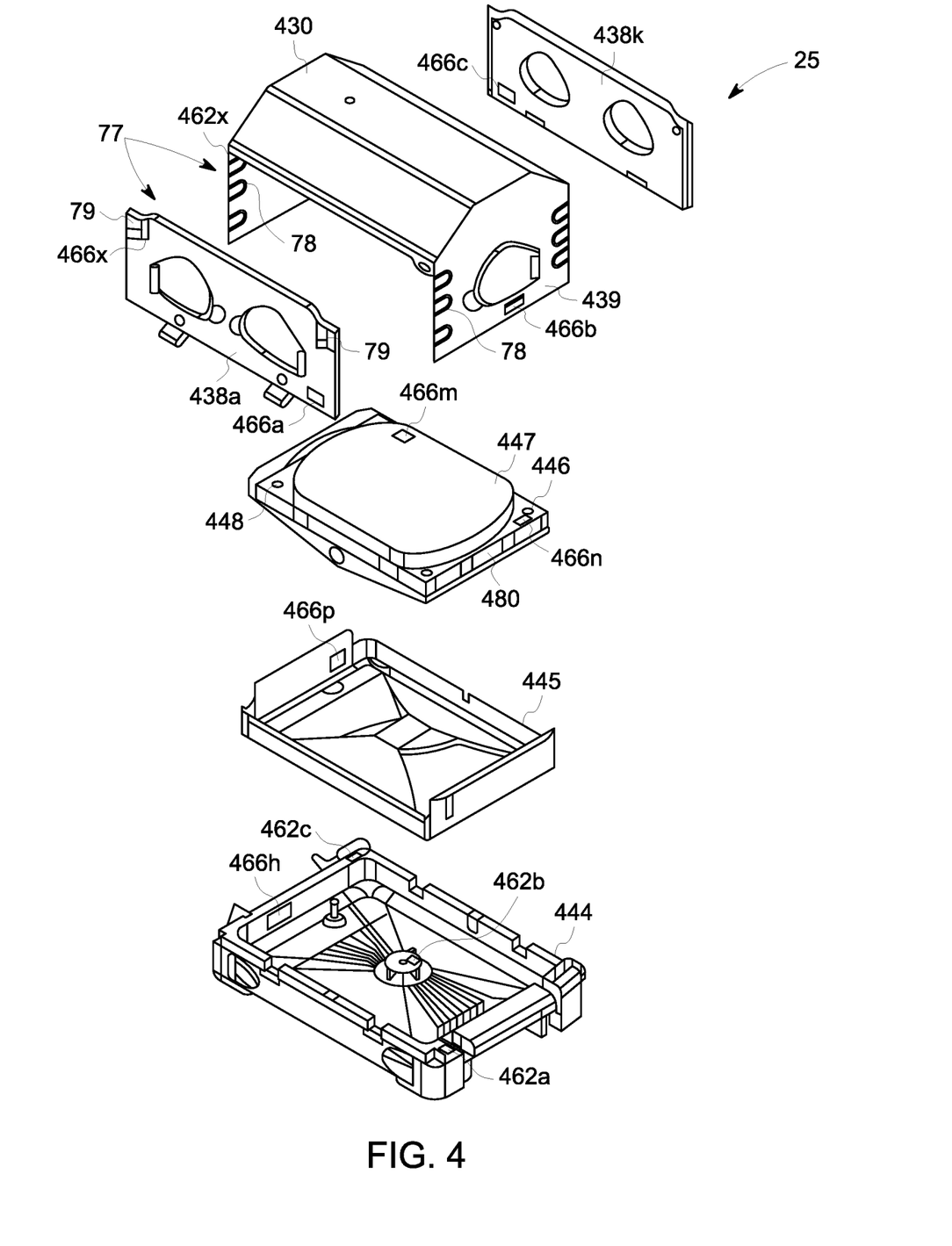
Figure 5:
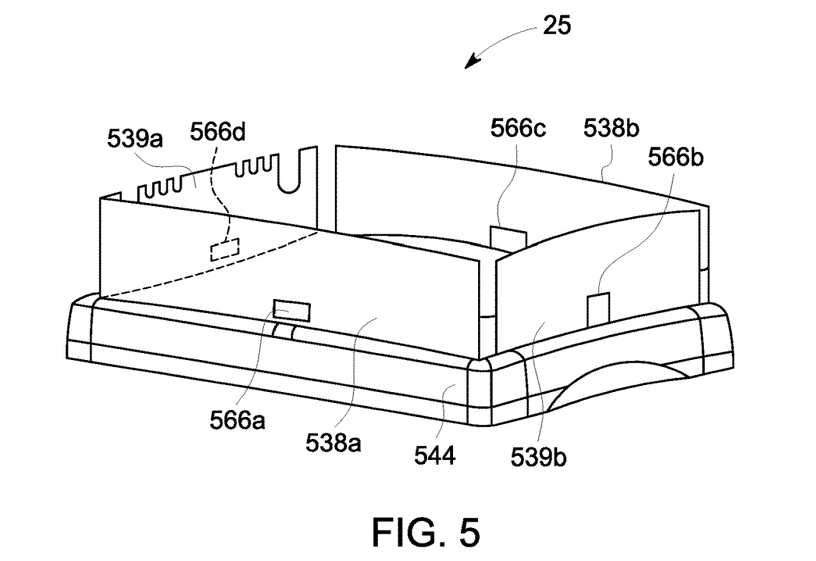
Figure 6:
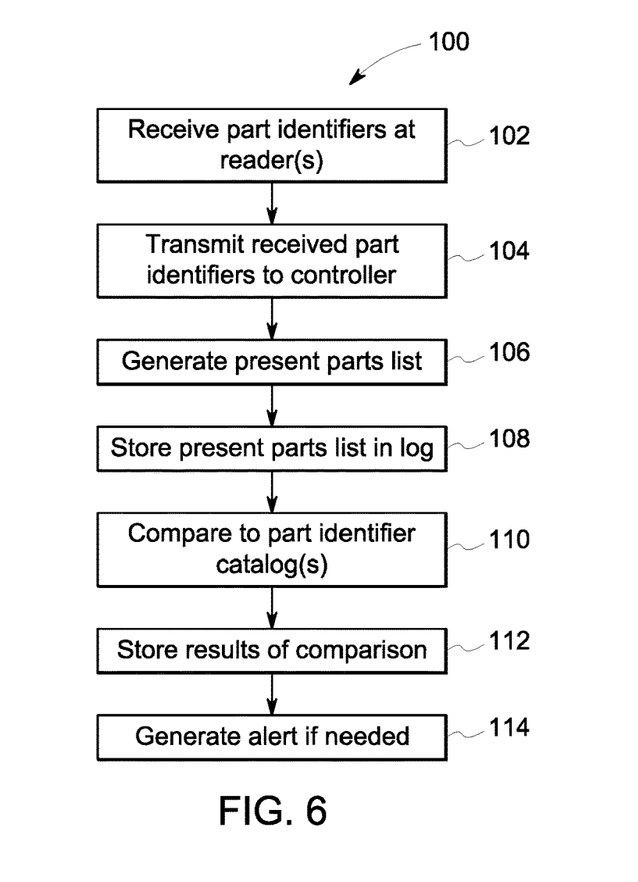
FIG. 6 is a flow chart exemplifying one embodiment of a method of tracking composition of a neonatal care system.

The transmission strength of the part identifiers 66 and/or the fields of the receiving readers 62 may be adjusted to provide particular detection capabilities and information regarding the position, composition, and/or arrangement of parts within the system 10. FIGS. 3-5 provide examples, where readers 62 and tags 66 are each strategically positioned to detect not only the presence of certain parts, but also the orientation and/or position of those parts. FIG. 3 depicts a housing 25 for a neonatal care system, where the housing 25 includes multiple walls 38 and 39 and a hood 30. The hood 30 includes a warmer cover 30' configured to cover a warmer 67, such as a radiant warmer. A portion of the housing 25 includes part tag 66 configured to transmit a part identifier that identifies the particular part within the part tracking system 60. Four walls are provided, including two side walls 338a and 338b and two end walls, including 339a and 339b. Each wall has its own part tag to identify that wall in its transmission to one or more of the part readers 62a-62c. The first side wall 338a includes a first part tag 366a, and the second side wall 338b3 includes part tag 366c. The first end wall 339a includes part tag 366d and the second end wall has part tag 366b. Additionally, part tag 366e is incorporated in fixed to the hood 330 and part tag 366f is in the heater cover 330' portion of the hood.

Each wall is configured to removably connect to a chassis 44 in some embodiments which is also removable from the incubator system 10. The chassis 44 may include one or more readers 62a-62c configured to receive the part identifiers transmitted by the part tags 66 in the various housing 25 elements, including the walls 38 and 39. The readers may be positioned and have range such that they only receive communication from the part tags 366 near that portion of the chassis 44. For example, each reader 62a and 62c on the ends of the chassis 44 may have a range configured to receive identifiers from the part tags of only one sidewall and one end wall, where the part tags are positioned on a portion of the wall such that when the respective wall 338 and 339 is correctly installed, each of the part tags 366a-366d is positioned near a corresponding reader 62a-62c. In the example, when the side wall 338a and the end wall 339b are properly installed, the part tags 366a and 366b are positioned in range of the reader 62a on the chassis 44. Likewise, when the side wall 338b and the end wall 339a are properly installed on the chassis 44, the respective tags 366c and 366d are within range of the reader 62c. Thus, if any of the walls 338 or 339 are installed backward or not installed on the correct side, or even not installed at all, then the appropriate readers 62a and 62c will not receive the transmission from the tags 366a-366d. For example, the readers 62a and 62b may have a range that is less than half the length L of the chassis, and in some embodiments the range may be half or less of the width W of the chassis 44. In certain embodiments, the range of the readers 62a and 62b may be only a few inches, such as less than 10 inches.

The ranges of the readers 62a-62c, and likewise the transmission strength of the various tags 366a-366f may be variously configured to provide the needed tracking function. For example, the readers 62a and 62c may be specifically configured for detecting presence or absence of the various walls installed on the chassis 44, and thus may have a range configured accordingly. Alternatively, if the readers 62a-62c configured to track a number of parts, some of which are further away from the respective reader 62a-62c, then the range may be bigger. In certain embodiments, the readers 62a-62c may have differing ranges. For example, readers 62a and 62c may have shorter ranges and be configured to track presence and absence of the adjacent walls, whereas part reader 62b may have a larger range and be configured to receive part identifiers from all parts in the housing 25, including part tags 366e and 366f on the hood 330. Thus, two or more of the part readers 62a-62c may be configured to receive a single part identifier from any one of the various tags 366a-366f.

In the depicted embodiments, FIGS. 3 and 4, the chassis 44 includes part readers 62a-62c. However, in other embodiments the part readers 62 may be incorporated elsewhere within the neonatal care system 10, such as on the base 12 or within the frame housing 52, or anywhere else. Referring to the example at FIG. 1, part reader 62d is positioned on the frame housing 52 and is configured to receive part identifier transmissions from one or more of the tags associated with parts that are installed within the neonatal care system 10. For example, the part tag 62d may be configured and positioned to receive part identifier from a part tag on incubator cover (not shown) configured to cover the housing 25 to reduce the amount of light transmitted into the neonatal care environment. In such an embodiment, the reader 62d may have a relatively short range, and the part tag on the housing may be positioned near a top end, and thus near the part reader 62d. In other embodiments, the part reader 62d may have a very long range extends or passed the end of the chassis 44, and thus may receive transmissions from all part tags on the platform 20 and the housing 25.

The neonatal care system 10 may be configured to receive various housing 25 elements, such as to convert the care system 10 into an incubator, a warmer, a hybrid, or to provide different heights or sizes of walls, hoods, etc. In certain embodiments, the system 10 may be configured to receive different chassis configured to form different housing types. Alternatively or additionally, each chassis may be configured to receive one or more different housing configurations. Thus, the tracking system may be configured to determine what type of housing configuration is installed on the care system 10, and also to determine whether the arrangement of various housing parts complies with an approved combination of parts to make sure that the housing 25 is constructed properly, whichever housing embodiment is selected. FIG. 4 depicts another housing 5 type, which is an incubator housing. The housing 25 includes two side walls 438a and 438b and an integrated hood for 30 and end walls 439 configured to connect with the side walls 438a and 438b to completely cover and surround the arranged compartment for the infant. Each housing 25 part includes a part tag 466. The first side wall 438a includes tag 466a and the second side wall 438b includes tag 466c. The integrated end wall 439 part includes tag 466b.

The housing 25 parts removably connect to the chassis 444 which includes three part readers 462a-462c, which may be variously configured as described above. In this embodiment, the chassis 444 also includes a part tag 466h which may be configured to communicate with a reader 62 positioned on the base or frame of the neonatal care system 10, or elsewhere. Thus, where the neonatal care system may be configured to receive different chassis types, the part tag 466h may be configured to identify the chassis type, which may then be tracked and analyzed as described herein to ensure, for example, that the various housing 25 parts and bed assembly parts are proper for that chassis 444 type.

The chassis 444 may be configured to receive various bed assemblies, which provides flexibility and configurability for different care environments accommodate neonatal care needs. In the depicted example, the bed assembly includes a pan 445 and a mattress assembly 446. The pan 445 connects to the chassis 444 and the mattress assembly 446 then connects to the pan 445. The pan 445 and the mattress assembly 446 has its own one or more part tags. Part tag 466p is configured to identify the pan 445. The mattress assembly 446 includes a mattress frame 448 and a mattress 447. In certain embodiments, the mattress 447 is removable from the mattress frame 448 and the mattress system 446 may be configured to accept and include various types of mattresses, depending on the infant care needs. Tag 446n identifies the mattress frame 448 and part tag 466m identifies the mattress 447.

In certain embodiments, the part tag 466m on the mattress 447 may be positioned asymmetrically on the mattress 447, and one or more of the part readers 462a-462c may have a range that enables determination of the orientation of the mattress 447. For example, one or more of the part readers 462a-462c may have a short detection range and position of the short range reader may be coordinated with that of the mattress tag 466m such that the mattress 447 is properly installed, the mattress tag 466m is within range of the particular short range reader 462 (or alternatively, deliberately not in range of a reader, where the system is configured with a reader configured to detect the tag 466m only if the mattress is incorrectly positioned). In the depicted example, part reader 262c may be configured with a range that captures the part identifier transmission from the mattress tag 466m when the mattress is properly installed with the correct orientation. However, if the mattress is installed backwards such that the part tag 466m is part of the foot side 480 of the mattress assembly 446, then the part tag 466m on the mattress is not within range of the reader 462c. Similarly, the wall part tags 466a-466c may be positioned in a way that is coordinated with the position of the readers 462a-462c such that orientation and installation position of the various walls can be determined. Comparison of the signals identified by the various readers 462a-462c can provide additional information, particularly where the readers are configured with a range that covers only a portion of the chassis 444 and housing 25.

In certain embodiments, part tags and readers may also be arranged to determine whether one or more of the side panels 438a and 438b are in an open or closed position. One or more of the side walls 438a and 438b may be hingeably connected such that they can swing open or closed as is standard in the relevant art. However, the inventors have recognized that a problem exists where side walls may not completely close such that a latching system 77 is unable to secure the side wall in a fully closed position. Incidents have occurred where a side wall 438a, for example, appears closed but is not fully latched, and thus can swing open and create an unsecured environment for the infant. The inventors have recognized that the tracking system can be configured to determine whether the side wall 438a, for example, is in the fully closed and locked position. A part reader 462x may be positioned on or adjacent to a latch receiver portion 78 of the latching system 77 and a part tag 466x may be correspondingly positioned on the side wall 438a such that it is on or adjacent to the latch portion 79 on the side wall 438a. The part reader 462x may be configured with a very short range such that it only detects the transmissions from the part tag 466x when the side panel 438a is in the fully closed position and the latch system 77 is engaged. For example, the part reader 462x may have a range of a few centimeters, or even less. In certain embodiments, the part reader 462x and the part tag 466x may be correspondingly configured such that they are only in range of one another when the latch portion 79 on the side panel 438a is contacting and engaged with the latch receiver portion 78 on the integrated hood 430 and side wall 439 element. In certain embodiments, the controller 50 may be configured to generate a door open alert when the part tag 466x is not detected by the part reader 462x.

FIG. 5 depicts another embodiment of a housing 25, which in this embodiment includes shorter walls, which may be appropriate for a warmer configuration, for example. In this example, the chassis 544 is removably connected to two side walls 538a and 538b and two end walls 539a and 539b. Each of the walls has a respective part tag 566a-566d identifying that wall. One or more part readers are positioned to receive part identifiers from each of the walls and to track the housing configuration assembled on the infant care system.

Where the infant care system is configured to receive multiple different combinations of parts, the controller 50 may be configured to compare a present parts list presenting all part identifiers transmitting at a given time or within a given period to one or more part schedules to verify that all necessary parts are present and that the parts that are present are proper and represent a proper combination. For example, various wall types may be assembled onto a particular chassis 44, 444, 544, as described above. Such walls may be different heights and/or different materials, and certain combinations of walls may not be appropriate for properly assembling a housing 25. Thus, the controller 50 may be configured to compare the present parts list to a part combination schedule 70c to make sure that the combination of walls assembled to the chassis represent an approved and proper combination of walls. Similarly, the present parts list may be compared to a necessary part schedule 70b to verify that part identifiers corresponding with each of the four walls are detected, and thus that the walls are present and properly installed (e.g., properly oriented and located on the correct side of the chassis 4, 44, 544). Alternatively or additionally, the present parts list may be compared to a permitted part schedule 70a, which may include all approved parts for the neonatal care system 10 to make sure that the wall is one that can be installed and used with the particular neonatal care system 10 and thus is not, for example, a counterfeit part or a part not designed for the neonatal care system 10.

FIGS. 6 through 9 depict embodiments of methods 100, portions thereof, of tracking composition of a neonatal care system 10. In the embodiment at FIG. 6, one or more part identifiers are received by one or more receivers at step 102. The part identifiers are then communicated to the controller at step 104. Such transmission may be by any wired or wireless means depending on the system configuration. A present parts list is then generated at step 106. As described above, the present parts list may represent all transmitting parts on the neonatal care system 10 at a given time, such as all parts of the neonatal care system for which a transmitted part identifier is received by the at least one part reader within a timed period of time. The present parts list may then be stored at step 108 such as in a log associating the present parts list with the corresponding time or time period represented thereby. Thus, the log may represent all transmitting parts installed on the neonatal care system 10 over time. Each present parts list, upon generation, may be compared to one or more part identifier catalogs at step 110. The result of the comparison is then stored at step 112. If comparison of the present parts list to the part identifier catalog reveals an abnormality or a mismatched, then an alert may be generated at step 114 in addition to storing the abnormality or mismatch in the log for the neonatal care system.

Figure 7:
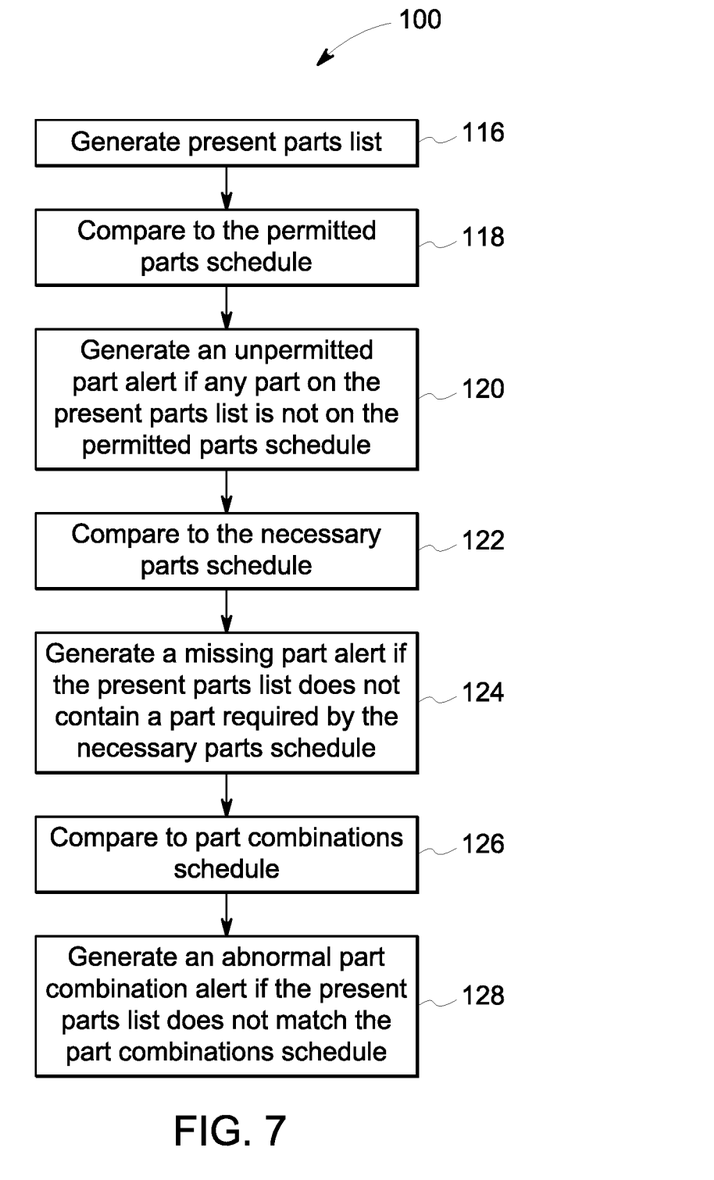
FIGS. 7-9 are flow charts exemplifying additional embodiments of methods, or portions thereof, of tracking composition of a neonatal care system.

FIG. 7 depicts exemplary logic for comparing the present parts list to the part identifier catalog. As described above, the part identifier catalog may include one or more schedules representing approved parts and assemblies for the neonatal care system 10. Once the present parts list is generated at step 116, it is compared to a permitted parts schedule 70a at step 118. As described above, the permitted parts schedule 70a represents parts that are approved for the neonatal care system 10. Any part on the present parts list is not on the permitted parts schedule 70a, then an unpermitted part alert is generated at step 120.

The present parts list is also compared to a necessary parts schedule at step 122. As described above, the necessary parts schedule 70b represents parts or collections of parts that are necessary for proper and safe operation of the neonatal care system. To provide just one example, a necessary parts schedule 70b may require a chassis and four walls (among other parts), which may be satisfied with various chassis and wall types. If the present parts list does not contain one or more parts required by the necessary parts schedule 70b, then a missing part alert is generated at step 124.

The present parts list is compared to a part combinations schedule 70c at step 126. As described above, the part combinations schedule 70c may represent approved combinations of parts. To provide one example, the part combinations schedule 70c may include various wall combinations for the housing 25. In another example, the part combinations schedule 70c may include various bedding assembly combinations. If the present parts list does not match the part combinations schedule 70c, then an abnormal part combination alert is generated. For example, if the four wall part identifiers in the present parts list does not match any of the wall part combinations represented in the part combinations schedule 70c, then an abnormal part combination alert may be generated at step 128, which in some embodiments may alert the clinician to the abnormal wall combination or otherwise provide instruction as to what abnormal part combination is detected. Thus, the part combinations schedule 70c may represent a multitude of different approved part combinations, and the controller 50 may be configured to determine whether the parts on the present parts list match any of the various part combinations represented in the part combinations schedule.

The controller 50 may be configured to generate the present parts list at various times or upon various triggers. For example, the controller 50 may be configured to generate the present parts list following a cleaning and assembly of the neonatal care system 10 and prior to engagement of the system for patient care. Alternatively or additionally, the controller 50 may be configured to generate the present parts list at regular intervals to monitor and track the part composition of the neonatal care system 10 at the regular intervals. In still other embodiments, the controller 50 may be configured to generate the present parts list any time a change occurs to the present parts list, such as when a part is added or removed to the system 10. In certain embodiments, the steps for comparing the present parts list to the part identifier catalog may be executed each time a present parts list is generated.

Figure 8:
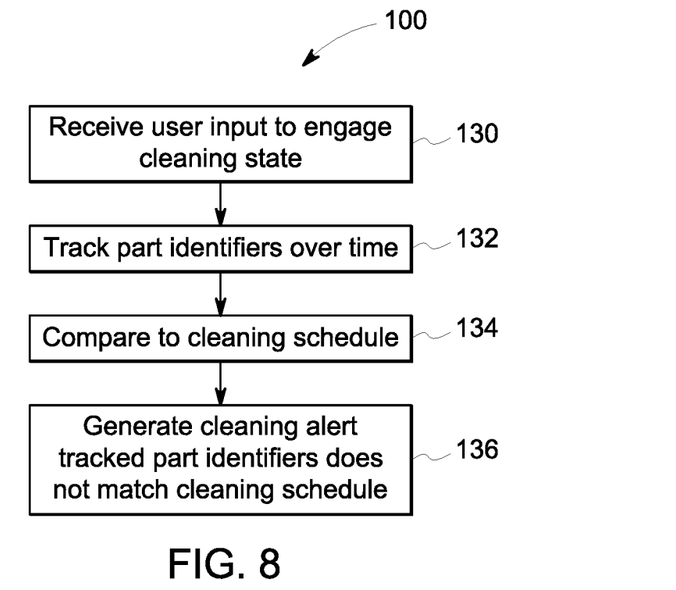
Figure 9:
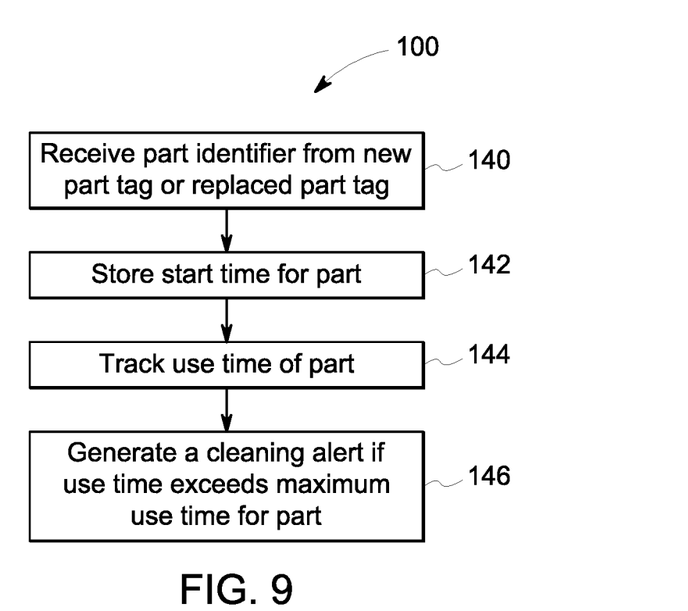

In certain embodiments, the part tracking system 60 may be configured to track cleaning of the neonatal care system 10 and track compliance with a cleaning schedule. FIGS. 8 and 9 depict exemplary logic for tracking cleaning. In certain embodiments, the controller 50 may be configured to determine the state the neonatal care system and conduct assessment and analysis of the present parts based thereon. One or more part schedules may be then associated with each state of the neonatal care system. For example, a different necessary part schedule may be associated with each state of the neonatal care system, and the controller 50 may be configured to select the appropriate necessary part schedule based on the determined state. Similarly, different part combination schedules, permitted part schedules, cleaning schedules, or other schedules may be associated with each state of the neonatal care system and selected and used by the controller 50 accordingly.

In certain examples, the state of the neonatal care system may be one of a cleaning state where the neonatal care system is being cleaned, a post-cleaning assembly state where the neonatal care system is being reassembled after cleaning, a use state where the neonatal care system is in use with the neonate, and a post-use state between the use state and the cleaning state. The controller may be configured with various logic for determining the state, which may include receipt of user input, such as via the display 54 or other user interface elements associated with the neonatal care system 10. The controller 50 may also be configured to assess current function of the neonatal care system to determine the state, such as whether temperature regulation and infant illogical monitoring functions are active or inactive, whether all parts are present, and in order of part assemblies or removal. For example, the part identifiers catalog may include a cleaning schedule, such as cleaning schedule 70d described above. The cleaning schedule may represent an order of part removal or part assembly for a cleaning process, and the controller 50 may be configured to detect a care state based on removal or assembly of certain parts by comparison to the cleaning schedule.

FIG. 8 represents one embodiment of a method 100 for tracking composition of the neonatal care system 10 during cleaning. A user input is received at step 130 to engage a cleaning state, such as via a user interface (e.g., display 54, which may be a touch screen display). The part identifiers received at the various readers are tracked over time, as represented at step 132. For example, present parts lists may be generated at regular or continuous intervals, or when any change in the detected part identifiers occurs, as described above. The part identifiers are then compared to the cleaning schedule at step 134. For example, any change in part identifiers may be compared to the cleaning schedule to assess whether all parts needing to be cleaned are removed from the infant care system 10 and/or that parts are removed or assembled in a particular order or within a particular required time period, such as to execute a particular cleaning step for at least a predetermined period of time. If the tracked part identifiers do not match the cleaning schedule, then a cleaning alert is generated at step 136.

FIG. 9 represents different steps that may be executed for tracking cleaning of the infant care system 10 and/or parts thereof. When a part identifier is received from a new part tag or a replaced part tag at step 40, a start time may be stored for the part at step 142. [Insert above: the depicted steps may be utilized to track a cleaning and/or replacement frequency for one or more parts.] For example, where a part is removed from the system 10 and cleaned, it will be replaced and redetected by one or more of the readers. Alternatively, where a part is removed from the system 10 and a new part is inserted in its place, then a new part tag is detected. In either event, a new start time is recorded for that part. Use time is then tracked, as represented in step 144, which is a period of time following the start time for the respective part and in which the respective part is continually or intermittently detected. If the use time exceeds a maximum use time for a particular part, then a cleaning alert may be generated at step 146. For example, the cleaning schedule 70c described above may include a maximum use time for one or more parts that may be assembled in the neonatal care system 10 and the use time may be compared thereto in order to assess whether a particular part is being used for too long without cleaning or replacement. To provide just a few examples, use time may be tracked for one-time use accessories or elements, such as air filters, disposable covers or beddings, a disposable mattress, or the like. Similarly, use time may be tracked for one or more of the reusable aspects that need intermittent cleaning, such as the mattress, parts of the humidifier system, bedding, or the like. The cleaning schedule may store an appropriate maximum use time for each such part and the controller 50 may be configured to track the use time of each part based on detected insertion and removable of that part.

We claim:

1. A neonatal care system being a neonatal incubator system or a neonatal warmer system comprising:
   a platform for supporting an infant;
   a plurality of part tags, each part tag on or in a part within the neonatal care system, wherein each of the plurality of part tags is configured to transmit a part identifier;
   at least one part reader configured to receive the part identifiers transmitted from the plurality of part tags;
   a controller configured to:
     store at least one part identifier catalog;
     receive the part identifiers from the part reader;
     compare the part identifiers generated by the plurality of part tags to the at least one part identifier catalog and generate an alert if any of the part identifiers does not match the at least one part identifier catalog.

2. The system of claim 1, wherein the plurality of part tags are each an RFID tag on or embedded in the part and the part reader is an RFID reader.

3. The system of claim 1, wherein the controller is configured to track at least one part identifier over time to determine whether a part has been cleaned.

4. The system of claim 1, further comprising a neonatal mattress on the platform containing a part tag that transmits a mattress identifier, wherein one of the at least one part reader is configured to be in range of the part tag in the neonatal mattress when the neonatal mattress is properly installed.

5. The system of claim 1, wherein the at least one part identifier catalog includes a permitted parts schedule representing parts that are approved for the neonatal care system.

6. The system of claim 1, wherein the controller is further configured to generate a present parts list for the neonatal care system representing all parts of the neonatal care system for which a transmitted part identifier is received by the at least one part reader.

7. The system of claim 6, wherein the at least one part identifier catalog includes a necessary parts schedule, wherein the controller is further configured to compare the present parts list to the necessary parts schedule and to generate an alert if any part in the necessary parts schedule is not in the present parts list.

8. The system of claim 7, wherein the at least one part identifier catalog includes a plurality of necessary parts schedules each associated with a state of the neonatal care system, wherein the controller is further configured to select one of the necessary part schedules based on a present state of the neonatal care system.

9. The system of claim 8, wherein the state of the neonatal care system is one of a cleaning state where the neonatal care system is being cleaned, a post-cleaning assembly state where the neonatal care system is being reassembled after cleaning, a use state where the neonatal care system is in use with a neonate, and a post-use state between the use state and the cleaning state.

10. The system of claim 6, wherein the at least one part identifier catalog includes a part combinations schedule for the neonatal care system, wherein the controller is further configured to compare the present parts list to the part combinations schedule and to generate an alert if the present parts list does not match the part combinations schedule.

11. The system of claim 10, wherein the plurality of part tags includes a plurality of wall part tags, each in one wall of the neonatal care system and configured to generate a wall identifier;
wherein one of the at least one part reader is configured to be in range of each of the plurality of wall part tags when each of the walls of the neonatal care system are properly installed;
wherein the part combinations schedule includes a plurality of expected combinations of wall identifiers for the neonatal care system; and
wherein the controller is configured to generate an alert if the wall identifiers from the plurality of wall part tags do not match any of the plurality of expected combinations of wall identifiers in the part combinations schedule.

12. The system of claim 11, wherein the controller is configured to select the necessary parts schedule based on a state of the neonatal care system.

13. The system of claim 1, wherein the controller is further configured to generate and store present parts list for the neonatal care system representing all parts of the neonatal care system for which a transmitted part identifier is received by the at least one part reader;
wherein the at least one part identifier catalog includes a necessary parts schedule; and
wherein the controller is further configured to compare the present parts list to the necessary parts schedule and to generate a missing parts alert if any part on the necessary parts schedule is not in the present parts list.

14. A method of tracking composition of a neonatal care system, wherein the neonatal care system is a neonatal incubator system or a neonatal warmer system, the method comprising:
providing a plurality of parts for theft neonatal care system, each part having a part tag configured to transmit a part identifier, and at least one part reader configured to receive the part identifiers transmitted from the plurality of part tags when the respective parts are placed in the neonatal care system;
with a controller:
receiving the part identifiers from the plurality of part tags at the at least one part reader;
generating a present parts list for the neonatal care system representing all parts of the neonatal care system for which the part identifier is received by the at least one part reader within a period of time; and
storing the present parts list in association with the period of time so as to track the composition of the neonatal care system.

15. The method of claim 14, further comprising comparing the present parts list to a permitted parts schedule representing parts that are approved for the neonatal care system and generating an alert if any part identifier on the present parts list is not on the permitted parts schedule.

16. The method of claim 14, further comprising generating a log of present parts lists for the neonatal care system over time.

17. The method of claim 14, further comprising storing a necessary parts schedule for permitted use of the neonatal care system, and, with the controller, comparing the present parts list to the necessary parts schedule and generating an alert if any part in the necessary parts schedule is not in the present parts list.

18. The method of claim 14, further comprising storing a part combinations schedule for the neonatal care system, and, with the controller, comparing the present parts list to the part combinations schedule and generating an alert if the present parts list does not match the part combinations schedule.

19. The method of claim 14, further comprising, with the controller, for at least one of the plurality of part tags, determining a length of time that the part containing the at least one of the plurality of part tags has been in the neonatal care system;
determining that the length of time exceeds a threshold length of time for that part;
generating an expired part alert.

* * * * *